United States Patent
Lauks

[19]

[11] Patent Number: 6,015,294
[45] Date of Patent: Jan. 18, 2000

[54] DENTAL IMPLANT

[76] Inventor: Nikola Lauks, Saalkamp 8, D-22397 Hamburg, Germany

[21] Appl. No.: 09/156,531

[22] Filed: Sep. 17, 1998

[30] Foreign Application Priority Data

Sep. 19, 1997 [DE] Germany .......................... 29716883 U

[51] Int. Cl.[7] ....................................................... A61C 8/00
[52] U.S. Cl. ................................................................. 433/173
[58] Field of Search .................................... 433/172, 173, 433/174, 175, 176

[56] References Cited

U.S. PATENT DOCUMENTS

| | | | |
|---|---|---|---|
| 2,745,180 | 5/1956 | Kiernan, Jr. ............................. | 433/175 |
| 4,728,331 | 3/1988 | Russier ................................... | 433/175 |
| 5,049,073 | 9/1991 | Lauks ...................................... | 433/173 |
| 5,133,662 | 7/1992 | Metcalfe ................................. | 433/176 |
| 5,433,607 | 7/1995 | Schmid et al. ......................... | 433/173 |
| 5,470,230 | 11/1995 | Daftary et al. ......................... | 433/173 |

FOREIGN PATENT DOCUMENTS 297 16 883  5/1998  Germany .

*Primary Examiner*—John J. Wilson
*Attorney, Agent, or Firm*—Herbert Dubno

[57] ABSTRACT

A dental implant has at least one and preferably a plurality of wedges extending from the end of the implant body opposite that provided with the superstructure for receiving the dental prosthesis. The wedge-shaped bodies penetrate into the spongiosa and allow the bore cavity for receiving the implant to be shorter and the drilling process less traumatic.

12 Claims, 3 Drawing Sheets

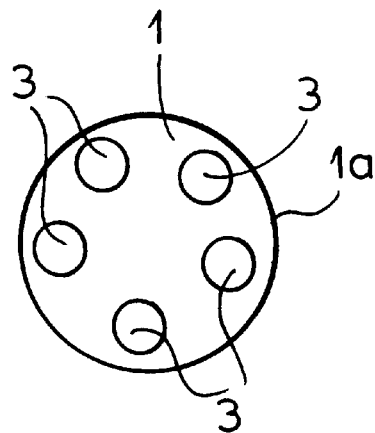
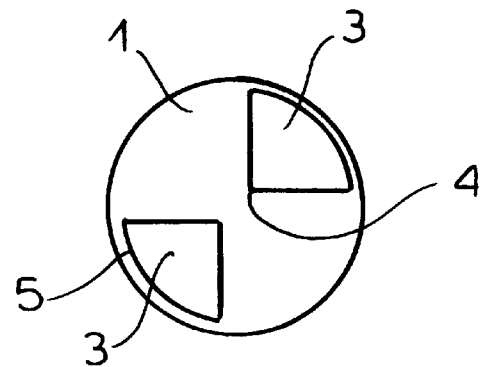
FIG.5　　　　　　　　FIG.6
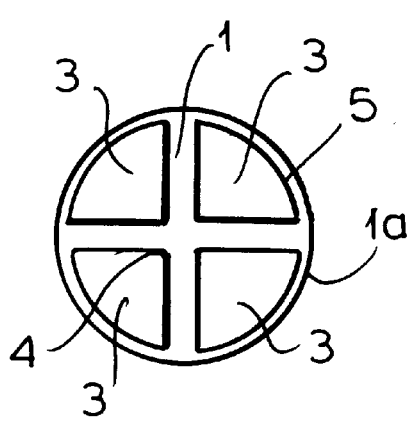
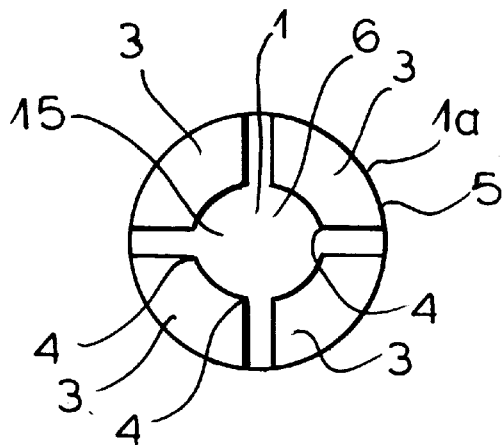
FIG.7　　　　　　　　FIG.8

DENTAL IMPLANT

FIELD OF THE INVENTION

The present invention relates to a dental implant and, more particularly, to a system for retaining a dental structure in the jaw of a patient.

BACKGROUND OF THE INVENTION

It has become increasingly important, in recent years, to provide a system for anchoring a dental structure, such as a crown, bridge or like array of teeth or a single tooth, in the jaw of a patient. For that purpose, a dental implant may be anchored in the bone tissue of the jaw.

In the past it has been common to form these jaw implants of a substantially cylindrical, conical or screw shaped member or in the form of a blade implant and to anchor the implant in the bone tissue by providing a bore or cavity in the bone tissue.

A superstructure is customarily attached, to the implant usually by means of a screw connection.

To facilitate the anchoring of the implant in the bone, the bone tissue may be induced to grow in and around the implant. In cylindrical implants, the implant diameter substantially matches the bore diameter or is slightly larger so that a press fit can be formed between the implant and the bone tissue. The bone structure may be such that the fit is unsatisfactory or there may be a poor fit as a result of some inaccuracy or failure in the formation of the bore so that the implant is not anchored with sufficient force in the bone tissue or the anchoring force is not uniform all around the implant. In such cases, loss of the implant is possible. If the press fit results in excessive pressure on the bone tissue, however, the latter may be damaged. This can give rise to local mortality of the bone tissue, can interfere with healing of the damage to the bone tissue caused by the implant and ultimately can also result in loss of the implant or some greater injury to the patient.

In cases in which the implant has the configuration of a screw and is anchored in the bone tissue by threading the implant into it, it has been found that resorption of the periimplant bone tissue can occur which must be compensated by new bone growth. This new bone growth, however, takes considerable time and, as a consequence, the period of healing after the insertion of an implant can be considerable.

It is also a drawback of the implant method that the bore may be drilled too deeply. In that case, the hollow of the bone may be penetrated and damage caused to the mandibular nerves.

Finally, in this regard, for each implant bone tissue must be removed to a depth which corresponds to the implant length so that surrounding bone tissue can be significantly traumatized.

OBJECTS OF THE INVENTION

It is, therefore, the principal object of the present invention to provide a dental implant for the purposes described which can insure healing of the implant in place with greater reliability then has hitherto been the case and which, in setting of the implant, will result in a significantly reduced traumatization of the bone tissue.

Another object of the invention is to provide an improved implant and dental structure which can be connected to the implant, which can be set in the jaw more readily and more effectively than earlier dental implants.

Still another object of this invention is to provide a dental implant which overcomes drawbacks of earlier dental implant systems.

SUMMARY OF THE INVENTION

These objects and others which will become more readily apparent hereinafter are attained, in accordance with the invention by providing the end of a dental implant opposite that which is formed with the superstructure with at least one wedge designed to be anchored in the bone tissue. When the implant has at least one wedge, the implant is set into the jaw so that this wedge engages in the marrow space of the bone without stressing the walls of the bore in the jaw so that at least the initial or primary stability is a result of the fact that the marrow tissue hugs the wedge or wedges or that the wedge or wedges fit snugly into the marrow tissue without loading or damaging the bone tissue forming the wall of the bore. The primary stability is thus independent of the snugness with which the implant is held by the wall of the bore or by screw threads or the like. The length of the bore can also be smaller than the total length of the implant and as a consequence the depth of damage to the bone tissue can be reduced and the danger that the hollow space of the bone tissue will be trepanned or that the mandibular nerves will be effected is greatly reduced.

With the invention a press fit with a high degree of force is unnecessary and bleeding of the tissue surrounding the implant is reduced. There is less traumatization of the bore wall also in part because of the time required for forming the bore is reduced.

According to a feature of the invention, at least two wedges are provided opposite one another or at least three wedges are provided in spaced relationship about a circle. In this case, a plurality of wedges are disposed in equispaced relationship about the longitudinal axis of the implant. In this manner, the primary stability is additionally insured because the bone tissue can grow between the wedges and, when the wedges penetrate into the marrow space, the marrow can pass into the crevices, grooves and channels between the wedges. In addition, the rotation of the implant about its longitudinal axis is prevented.

Utilizing two or more wedges in the marrow space of the bone, the spongiosa can be forced into the interior of the implant, namely, the aforementioned channels, to block rotation. Upon healing of the implant, posts or the structure can be screwed into the latter. In cases in which mechanical action could damage the freshly healed implant, the antirotation blockage formed by the penetration of the spongiosa into the crevices significantly reduces the trauma. Implant loss is practically precluded.

BRIEF DESCRIPTION OF THE DRAWING

The above and other objects, features, and advantages will become more readily apparent from the following description, reference being made to the accompanying drawing in which:

FIG. 5 is an end view of an implant with five circular cross section wedges disposed along a circle surrounding the longitudinal axis of the implant;

FIG. 6 is an end view of an embodiment having two polygonal cross section wedges with outer rounded surfaces;

FIG. 7 is an end view of an implant with four polygonal wedges with their outer surfaces rounded;

FIG. 8 is an end view of an implant having four polygonal wedges with their outer surfaces rounded and having a central bore;

SPECIFIC DESCRIPTION

Figure 11:
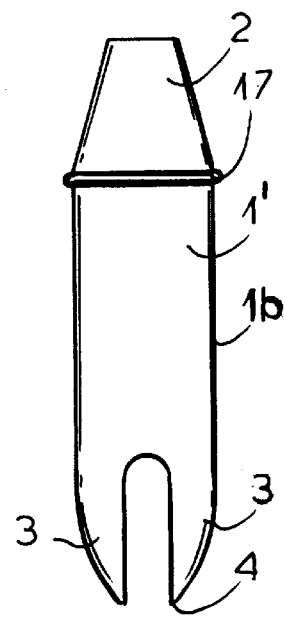
FIG. 11 is a view similar to FIG. 3 of an implant which is tapered away from the superstructure.

A jaw implant 1 (FIG. 1) can comprise a cylindrical implant body 1a or, as shown in FIG. 11 for the implant 1', a conical implant body 1b converging away from the superstructure 2 and which is intended to be anchored in a jaw bone 7. The implant 1 (FIG. 1) has at its end opposite the superstructure 2, a wedge 3 of circular cross section which is tapered toward the spongiosa 12, 13 of the jawbone. The superstructure 2 can be any conventional superstructure for attaching a dental implant such as a crown. As can be seen from FIG. 2, two or more such wedge members 3 can be provided and these wedge members can be of round, triangular or polygonal cross section. It has been found to be advantageous to provide the wedges 3 with cutting edges 4 which can penetrate into the spongiosa past the end of the implant bore.

Figure 2:
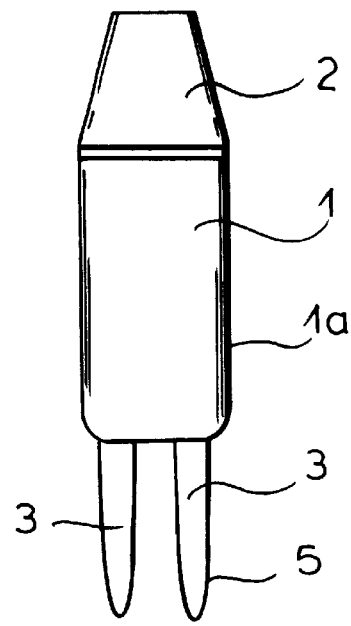
FIG. 2 is a side elevational view of a jaw implant with a superstructure and two wedges each of circular cross section.
Figure 3:
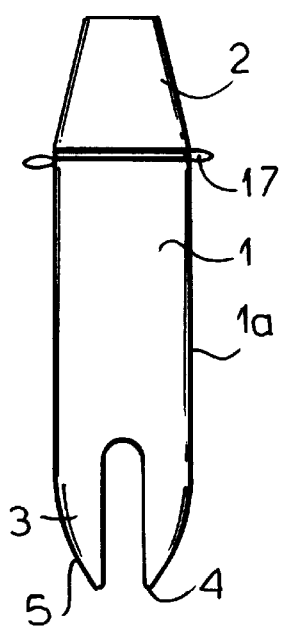
FIG. 3 is a similar view of a jaw implant having two wedges of polygonal cross section.
Figure 4:
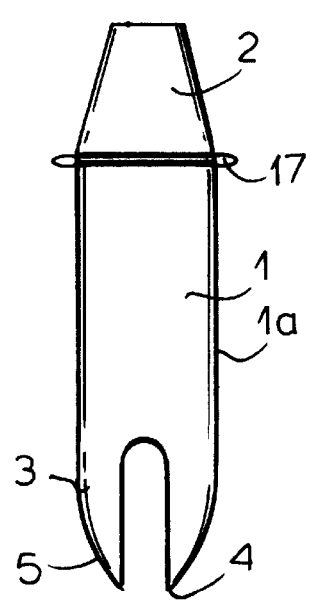
FIG. 4 is a side elevational view of a jaw implant with a superstructure and four wedges, each of circular cross section, two of those wedges being broken away.

Furthermore, at least outer surfaces of the wedges 3 are rounded as has been shown in FIGS. 2 and 3 by way of example. In FIG. 4, the two wedges 3 behind those in the foreground are not visible (compare FIG. 7).

The cutting edges serve to cut through particles of the spongiosa 13 which otherwise might obstruct full seating of the implant.

Figure 1:
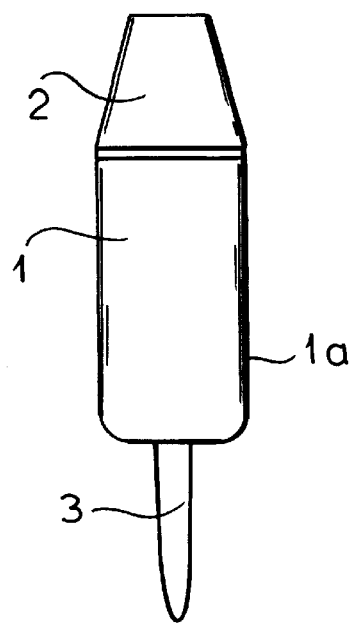
FIG. 1 is a side elevational view of a jaw implant with a superstructure and a central wedge of circular cross section.

In FIGS. 3, 4, 6, 7 and 8 and in FIG. 11, the wedges are polygonal in cross section rather than being formed as pegs as is the case with the wedges of FIGS. 1, 2 and 5.

Figure 10:
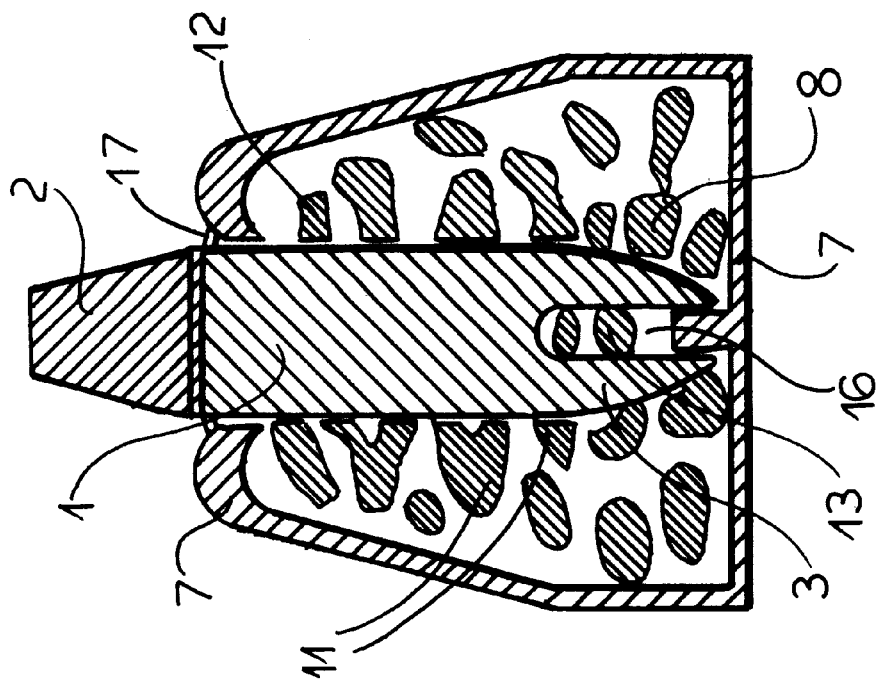
FIG. 10 is a cross sectional view through an implant in place in the jaw bone and having four wedges in the pattern of the wedges of FIG. 7.
Figure 9:
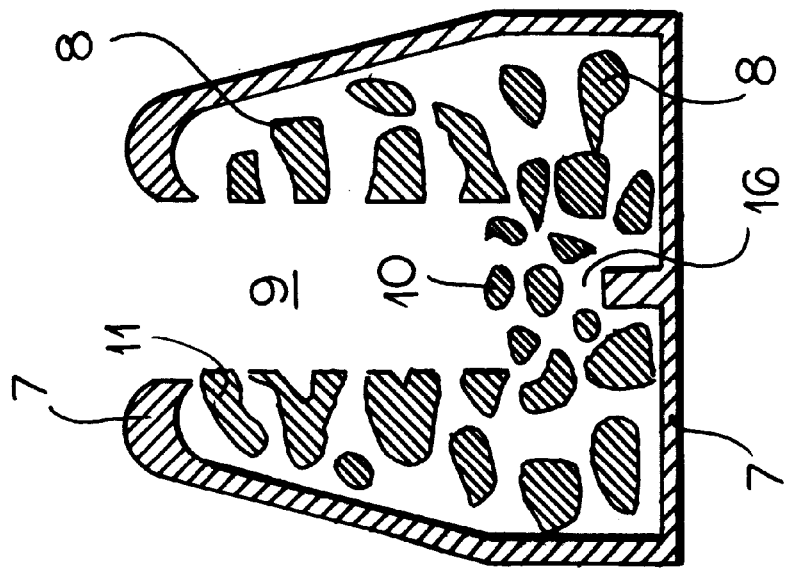
FIG. 9 is a cross section through a jaw bone formed with an implant bore.

As can be seen from FIGS. 9 and 10, a bore 9 can be formed in the bone 7 to a depth subsequently equal to the height of the implant body 1a. The implant is driven into the hole, however, so that the wedges 3 penetrate the spongiosa 13 in the region 16 below the bottom 10 of the hole. The spongiosa particles are cut apart by the cutting edges 4 of the implant and, since the depth of the hole 9 is limited, the danger of trepanning of the mandibular nerve, for example, is reduced. It has been found that the implant is held tightly not only by the spongiosa 12 of the outer wall of the implant body but by the grip of the spongiosa on the wedges. Bleeding is limited and because of the limited depth of drilling, the bone tissue 12 and 13 is last traumatized in part because less time is required to drill the cavity. When a plurality of wedges are used (FIGS. 2 through 8 and 11) and the wedges are arrayed around the longitudinal axis of the implant, rotation of the implant is restricted. The spongiosa passes between the wedges 13 (FIG. 10) and even up into a bore 15 which may be provided in the implant body (FIG. 8) and thereby remains vital. Healing is thereby facilitated. A loss of the implant by twisting of it in the bore is precluded.

A radial flange 17 may be provided at the superstructure end of the body 1a (FIGS. 3 and 4) to seal the bore cavity and reduce the penetration of microorganisms as is the case in EP 0 370 522 B1.

I claim:

1. A jaw implant for superstructure adapted to receive a dental prosthesis, comprising:

an elongated implant body formed at one end with a superstructure adapted to receive a dental prosthesis and an opposite end; and at least three elongated wedges arrayed along a circle centered on a longitudinal axis of the body, extending from said other end, and adapted to be anchored in spongiosa of the jaw upon seating of said implant in a bore in a bone of the jaw of a patient.

2. The jaw implant defined in claim 1 wherein each of said wedges is formed with a cutting edge at an extremity thereof remote from said body.

3. The jaw implant defined in claim 1 wherein each of said wedges has a circular cross section.

4. The jaw implant defined in claim 1 wherein each of said wedges has a polygonal cross section.

5. The jaw implant defined in claim 4 wherein each of said wedges is of substantially triangular cross section.

6. The jaw implant defined in claim 1 wherein each of said wedges has at least one outwardly rounded surface.

7. The jaw implant defined in claim 1 wherein said body at said opposite end is formed with a bore along a longitudinal axis of the body.

8. The jaw implant defined in claim 1 wherein said body is of generally round cross section.

9. The jaw implant defined in claim 1 wherein said body is generally cylindrical or cartridge shaped.

10. The jaw implant defined in claim 1 wherein said body is of generally conical configuration and is tapered away from said superstructure.

11. The jaw implant defined in claim 1 wherein said body is formed at said one end with an annular flange.

12. A jaw implant for superstructure adapted to receive a dental prosthesis, comprising:

an elongated implant body formed at one end with a superstructure adapted to receive a dental prosthesis and an opposite end;

four elongated wedges arrayed along a circle centered on a longitudinal axis of the body and adapted to be anchored in spongiosa of the jaw upon seating of said implant in a bore drilled into bone of the jaw of a patient, said implant being fully received in said bore without a press fit against said bone, each of said wedges is formed with a cutting edge at an extremity thereof remote from said body, said wedges each having outwardly rounded outer surfaces; and an outwardly extending flange at said one end at least partly recessed in said bone and sealing said bore against the exterior.

* * * * *